United States Patent [19]

Ghosh

[11] 4,396,402

[45] * Aug. 2, 1983

[54] GAS PRODUCTION BY ACCELERATED BIOLEACHING OF ORGANIC MATERIALS

[75] Inventor: Sambhunath Ghosh, Homewood, Ill.

[73] Assignee: Institute of Gas Technology, Chicago, Ill.

[*] Notice: The portion of the term of this patent subsequent to Apr. 6, 1999, has been disclaimed.

[21] Appl. No.: 365,456

[22] Filed: Apr. 5, 1982

Related U.S. Application Data

[63] Continuation-in-part of Ser. No. 161,922, Jun. 23, 1980, Pat. No. 4,323,367.

[51] Int. Cl.³ .......................... C02F 11/04; C02F 5/02
[52] U.S. Cl. ..................................... 48/197 A; 48/209; 48/603; 48/613; 48/747; 48/901; 48/926; 48/129; 48/167
[58] Field of Search ............. 48/197 A, 209; 435/167; 210/603, 613, 747, 901, 926; 405/124

[56] References Cited

U.S. PATENT DOCUMENTS

| | | | |
|---|---|---|---|
| 2,572,767 | 10/1901 | Schlenz | 210/603 |
| 3,705,851 | 12/1972 | Brauer | 210/747 |
| 3,732,697 | 5/1973 | Dickson | 405/129 |
| 3,846,292 | 11/1974 | LeCompte | 210/926 |
| 4,022,665 | 5/1977 | Ghosh et al. | 435/167 |
| 4,323,367 | 4/1982 | Ghosh | 210/901 |

Primary Examiner—Peter F. Kratz
Attorney, Agent, or Firm—Thomas W. Speckman

[57] ABSTRACT

A process for gas production and accelerated bioleaching of organic materials by acid forming bacteria in beds of organic solids, such as landfills, passing the leachate of hydrolysis and liquefaction products of microbial action of the microorganisms with the organic material to an acid phase digestion zone to regenerate an activated culture of acid forming microorganisms for recirculation to the bioleaching zone. The supernatant from the acid phase digestion zone may be passed to a methane phase digestion zone operated under conditions to produce methane rich gas. The supernatant from the methane phase digestion zone containing nutrients for the acid forming microorganisms and added sewage sludge or other desired nutrient materials may be circulated to the acid phase digestion zone or to the bioleaching zone. Low Btu gas is withdrawn from the acid phase digestion zone while high Btu gas is withdrawn from the methane phase digestion zone and may be upgraded for use in SNG. The process of this invention is applicable to small as well as large beds of organic solids, such as waste landfills, provides simultaneous disposal of municipal solid waste and sewage sludge or other aqueous organic waste in a landfill which may be stabilized much more quickly than an uncontrolled landfill as presently utilized.

24 Claims, 2 Drawing Figures

GAS PRODUCTION BY ACCELERATED BIOLEACHING OF ORGANIC MATERIALS

CROSS REFERENCE TO RELATED APPLICATION

This application is a continuation-in-part of my application Ser. No. 161,922, filed June 23, 1980, issued Apr. 6, 1982 as U.S. Pat. No. 4,323,367.

BACKGROUND OF THE INVENTION

1. Field of the Invention

This invention relates to improved production of gas, particularly methane, by accelerated bioleaching of organic materials, such as from sanitary landfills or other confined deposits of organic matter.

2. Description of the Prior Art

Methane producing anaerobic digestion is well known and two-phase anaerobic digestion is known to the art and further disclosed in U.S. Pat. No. 4,022,665. Methane production by anaerobic digestion of garbage utilizing a liquor from anaerobic sewage sludge digestion is taught by U.S. Pat. No. 2,572,767.

Sanitary landfills formed by filling a land area with successive layers of solid waste, principally household waste, and layers of earth or soil are well known. The uncontrolled landfill depends upon natural biological action, precipitation and climate to effect decomposition. In areas where oxygen is present, the decomposition will be aerobic and in areas where little oxygen is present, such as at the deeper depths, decomposition will be slower and anaerobic producing methane containing gas. Initially, there is no methane production from the landfill and it increases very slowly with time to an amount representing only about 15 to 20 percent of the total potential production after many years. The formed methane is an explosion or fire hazard and may migrate to buildings or structures several hundred feet from the landfill if not removed from the landfill. Further, the natural precipitation draining out of the landfill may carry highly toxic contaminated water to contaminate underground water supplies, surface streams and wells. Due to the very slow stabilization, the uncontrolled landfill is not usable for other purposes for long periods of time and thus, particularly near metropolitan areas, represents a large waste of land resources.

One approach to rendering waste disposal landfills safer is suggested by U.S. Pat. No. 3,586,624 which teaches a liquid impervious containment of the lower portion of the landfill with continuous flow of water through the landfill to accelerate the decomposition, decrease the fire hazard and flush contaminants from the landfill in a controlled manner. The water drained from the landfill may be treated for removal of contaminants and recycled to the landfill. The combination of refuse with earth and industrial liquid wastes such as asphalts with earth to avoid liquid movement are taught by U.S. Pat. Nos. 3,705,851 and 3,732,697, respectively.

In the past, methane gas has been frequently vented and flared from concentrations of organic wastes, such as landfills, as a safety precaution. However, in recent years and especially in view of energy conservation, the recovery and utilization of methane from sanitary landfills and desirability of early utilization of the landfill area for other purposes has been recognized. "Methane Production, Recovery, and Utilization from Landfills," James, S. C. and Rhyne, C. W., Symposium Papers on Energy from Biomass and Wastes, Washington, D.C., Aug. 14–18, 1978, pgs. 317–324, and "Recovery and Utilization of Methane Gas from a Sanitary Landfill—City of Industry, Calif.," Stearns, R. P., Wright, T. D. and Brecher, M., Symposium Papers on Energy from Biomass and Wastes, Washington, D.C., Aug. 14–18, 1978, pgs. 325–343. Presently methane is most frequently recovered from landfills by pipes extending into the landfill and transporting the methane containing gas formed within the landfill to a collecting area for further treatment.

In the United States, about 1151 million tons (dry) of organic wastes are generated annually in the form of municipal solid waste, agricultural residue, manure, logging and wood manufacturing residues, municipal sludge solids, industrial organic wastes and miscellaneous organic wastes representing production potential of 11.8 trillion SCF/yr. of substitute natural gas (SNG). The most readily available solid waste for energy recovery is municipal solid waste estimated to be currently generated at about 260 million tons per year in the United States. Additionally, urban areas in the United States produce about 25 million tons (dry) per year of organic waste solids in sewage sludge. These wastes have presented intractable waste management and disposal problems and represent continuing loss of energy resources.

SUMMARY OF THE INVENTION

This invention relates to a process for improved gas production providing higher gas production rates and yields by accelerated bioleaching of organic wastes, such as organic wastes in situ in substantially sealed landfills. Methane producing anaerobic digestion systems utilize acid forming bacteria and methane producing organisms as are well known to be employed to produce methane from sewage sludge and are suitable for use in the process of this invention. Two-phase digestion is used under controlled digester conditions in the process of this invention, that is, acid phase digestion operated at mesophilic or thermophilic conditions to promote the growth of the acid forming bacteria and a second methane phase digestion operated at mesophilic or thermophilic conditions to promote the growth of the methane producing organisms. In the process of this invention organic material in a bioleaching zone is contacted with an aqueous activated culture of hydrolytic and liquefying anaerobic microorganisms under growth conditions to produce a bioleachate of hydrolysis and liquefaction products of microbial action of the microorganisms with the organic material. The bioleachate and the deactivated acid forming bacteria are passed from the bioleaching zone to an acid phase digester to regenerate the activated culture of hydrolytic and liquefying anaerobic microorganisms for recirculation to the bioleaching zone. The supernatant from the acid phase digester is passed to the methane phase digester operated under conditions to produce gas rich in methane. The supernatant from the methane phase digester, containing nutrients for the acid forming microorganisms, is returned to the acid phase digester or mixed with the activated culture of hydrolytic and liquefying anaerobic microorganisms from the acid phase digester and recirculated to contacting organic material in the bioleaching zone. Low Btu gas is withdrawn from the acid phase digester and may also be withdrawn from the bioleaching zone from time to time while high Btu gas is withdrawn from the methane phase digester for direct use or upgrading for use as substitute natural gas (SNG). Sewage sludge or other organic waste materials may be added to the bioleaching zone to increase the biological activity in the bioleaching zone, improve the nutrient balance and to dispose of the organic waste.

The terminology "bioleaching zone" as used in this disclosure and claims means any organic-rich material in a bed type configuration capable of contact by a liquid transporting microorganisms to produce a bioleachate of hydrolysis and liquefaction products of microbial action of the microorganisms with the organic material. One important type of bioleaching zone is a substantially sealed landfill which is contacted in situ with an aqueous activated culture of microorganisms as more fully disclosed in my prior application to issue as U.S. Pat. No. 4,323,367, the disclosure of which is fully incorporated herein by reference. Other suitable bioleaching zones may be used, such as beds of organic-rich materials in reactor vessels, dried lake beds, underground cavities, and the like. The bed may be operated with no liquid pool containment, as a partially flooded system, or as a fully flooded system.

The process of this invention provides rapid onset of bioconversion, increased gas production rate and higher concentrations of methane resulting in stabilized bioleaching zones available for other use much sooner than conventional organic conversion zones, such as landfills. In conventional landfills, biological gasification is severely retarded and there is a long time lag between closing of the landfill and onset of active methane fermentation, which then continues at very slow rates and in uncontrolled manners for many years. Further, the methane gas formed in the landfill migrates both vertically and laterally in an uncontrolled fashion causing a very hazardous situation. These disadvantages apply equally to other organic conversion zones.

The process of this invention greatly decreases the formation of methane in the bioleaching zone itself, and enhances overall energy production from the organic material by operation of two-phase digestion under controlled conditions.

It is an object of this invention to provide a process for improved gas production from organic conversion of solid organic materials.

It is another object of this invention to reduce fire and explosion hazards and pollution of areas surrounding solid organic waste conversion zones, such as landfills.

It is still another object of this invention to increase the methane content of gaseous products produced by anaerobic digestion based upon solid organic waste landfills.

It is yet another object of this invention to provide a process which is suitable for a wide variety of sizes of bioleaching zones, such as landfills, applicable to small as well as large organic waste landfills.

It is still another object of this invention to provide simultaneous disposal of municipal solid waste and sewage sludge or other aqueous organic waste in a substantially sealed landfill.

It is another object of this invention to provide a process for improved methane and useful chemical production by production of a bioleachate of hydrolysis and liquefaction products of anaerobic microbial action in beds of solid organic materials which may be operated with no liquid pool containment, as a partially flooded system, or as a fully flooded system.

BRIEF DESCRIPTION OF THE DRAWINGS

These and other objects, advantages and features of this invention will be apparent from the description together with the drawings wherein.

DESCRIPTION OF THE PREFERRED EMBODIMENTS

The process of this invention is applicable to beds of all types of organic materials. By the term "organic materials" as used in this disclosure and the appended claims, I mean all types of hydrocabonaceous organic materials including sewage sludge, animal waste, municipal waste, industrial waste, forestry waste, agricultural waste, fossil materials, fresh or salt water and land based biomass, and the like. By forestry waste and agricultural waste I mean to include portions of plants after some physical or chemical treatment, usually not including the entire plant, for example, stumps from logging, sawdust, wood chips, corn stalks, corncobs, bagasse and the like. By fossil materials, I mean to include peat, oil shale, tar sands and the like. Such organic materials may be mixtures of any of the above specific materials.

Municipal solid waste beds, such as landfills, constitute an important application of the process of this invention. Treatment of municipal solid waste and industrial solid waste for removal of undesired material such as glass, metals, plastics, stones, and the like, is well known to the art. Municipal solid waste contains over 50 weight percent (dry) cellulosics. Exemplary average composition of raw municipal solid waste is shown in Table I for municipal solid waste collected in Indianapolis, Ind.

TABLE I

| Components | Weight % dry |
|---|---|
| Paper Products | 45.7 |
| Wood | 2.1 |
| Textiles and Rags | 1.9 |
| Food and Garden Wastes | 10.9 |
| Total Cellulosics | 60.6 |
| Metallics | 13.6 |
| Glass, Ceramics, etc. | 16.6 |
| Dirt, Ash, Rocks | 3.0 |
| Plastics | 2.1 |
| Bulky Materials | 3.0 |
| Rubber and Leather | 1.1 |
| Total Non-Cellulosics | 39.4 |

The municipal solid waste is preferably shredded followed by magnetic separation of ferrous metals to reduce the bed volume and permit recovery of the ferrous metal. It is also preferred to separate glass from the waste also to reduce the bed volume and provide materials recovery for recycling.

Figure 1:
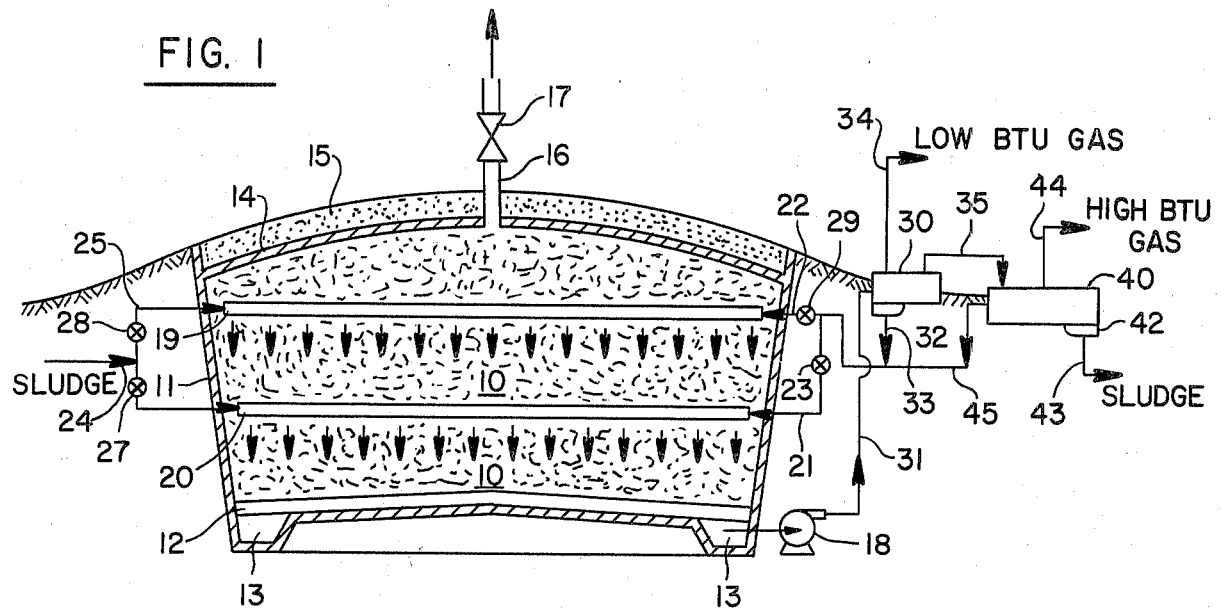
FIG. 1 is a sectional schematic view of a bioleaching zone of a bed of solid organic materials and gas production digesters according to this invention.

The bed volume to be filled with organic material is isolated from its surroundings, such as in the case of a landfill or subterranean cavity from ground water and surrounding soil formations using a liner for a landfill or subterranean cavity as shown in FIG. 1 may be any suitable barrier such as compacted clay, asphalt or other commercially available liner materials. The floor has collection drain 12 leading to sump 13 for recovery of the liquid leachate. The organic waste is spread and compacted in layers, 6 to 8 foot lifts, by conventional methods of constructing sanitary landfills. Collection drain 12 is preferably surrounded with crushed stone to enhance the liquid flow to the collection drain. During filling of the bed with organic material, such as organic waste 10, liquid distribution means, shown in FIG. 1 as pipes 20 and 19, are put into place to assure distribution of liquid throughout the landfill volume. The liquid distributiion means may include any arrangement of pipes or conduits with suitable holes or other means for distributing liquid, including liquid-solid slurries, both horizontally and vertically throughout the bed volume. When the bed or landfill is full of organic material, such as organic waste, top liner 14 and compact soil 15 is put into place to substantially seal the bed in the case of a landfill. Gas withdrawal pipe 16 having valve 17 is provided to withdraw any low Btu gas collecting at the top of the bed or bioleaching zone.

Bioconversion of the organic material is achieved by contacting the organic material with an aqueous activated culture of hydrolytic and liquefying anaerobic microorganisms under growth conditions to produce a bioleachate of hydrolysis and liquefaction products of microbial action of the microorganisms with the material in the bed or bioleaching zone. The active culture also contains desired nutrients for the hydrolytic and liquefying anaerobic microorganisms and by continued application of the activated microorganisms, moisture and nutrients, the bed or bioleaching zone is transformed into a medium supporting the growth of the hydrolytic and liquefying microorganisms. Growth and continued supply of the acid forming microorganisms may be enhanced by also supplying to the bioleaching zone aqueous liquid organic waste such as sewage sludge.

Any active methane producing mesophilic or thermophilic anaerobic digestion system may be used in the process of this invention. Methane-producing anaerobic systems utilizing acid forming bacteria and methane-producing organisms as are well known to be employed to produce methane from sewage sludge can be employed in practice of the present invention. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385–416, Pergamon Press (1969). As set forth in that review, the principal suitable acid forming bacteria include species from genera including Aerobacter, Aeromonas, Alcaligenes, Bacillus, Bacteroides, Clostridium, Escherichia, Klebsiella, Leptospira, Micrococcus, Neisseria, Paracolobactrum, Proteus, Pseudomonas, Rhodopseudomonas, Sarcina, Serratia, Streptococcus and Streptomyces. Exemplary methane-producing organisms suitable for use in the present invention include members of Methanobacterium, Methanococcus and Methanosarcina, specific members being *Methanobacterium formicicum, Methanosarcina barkerii, Methanobacterium omelianskii, Methanococcus vannielii, Methanobacterium sohngenii, Methanosarcina methanica, Methanococcus mazei, Methanobacterium suboxydans* and *Methanobacterium propionicum.* It is usually preferred to use mixed cultures to obtain the most complete fermentation action. Nutritional balance and pH adjustments may be made to the anaerobic system as is known to the art to optimize hydrolytic and liquefying action or methane production from the culture used, dependent upon the phase of the process.

The growth of the acid forming bacteria in the organic material in the bioleaching zone is promoted by maintaining a low pH of the introduced culture of about 4 to 7 and high throughput rates, for example, displacement of the pore volume liquid in about 1 hour to 5 days. As the aqueous culture moves down through the organic material bed, the microbial action extracts and captures the hydrolysis and liquefaction products of the organic waste to produce a bioleachate. The bioleachate and deactivated acid forming organisms may be collected by a system of riser pipes and underdrains within the bed for passage to an acid phase digester. Thus, the principal bioactivity in the bioleaching zone is the formation of the bioleachate and not the production of methane gas. Some low Btu gas and smaller amounts of methane may be produced in the bioleaching zone and may be removed from time to time by gas withdrawal pipe 16, but wells as used in the past for gas recovery from landfills are not necessary nor desirable. The relatively high rates of liquid throughput or the partially or fully flooded condition of the bioleaching zone provide removal of reaction products and toxicants from the bed.

The boileachate and deactivated acid forming microorganisms collected in sump 13, shown in FIG. 1, are transported by pump 18 through conduit 31 to acid phase digester 30. The digestion system which serves as a generator of activated acid forming microorganisms and gasification of the bioleachate is preferably a two phase digester system with a first digester operated under conditions promoting the growth of acid forming microorganisms and the second digester operated under conditions promoting the growth of methane forming microorganisms. By two phase digester system, I mean one having an acid phase zone and a methane phase zone which may be in a single or multiple overall containment vessels. Two phase anaerobic digestion is known to the art and is further disclosed in U.S. Pat. No. 4,022,665. The digesters shown in FIG. 1 may be closed-loop plug flow digesters with built-in settling systems to facilitate the withdrawal of activated cultures, the digesters being more fully described and shown in FIGS. 3 and 4 of U.S. Pat. No. 4,323,367.

The acid phase digester 30 is fed the bioleachate and deactivated acid forming microorganisms through conduit 31. Anaerobic digestion is carried out in the acid phase digester under mesophilic, 15° to 45° C., or thermophilic, 45° to 70° C., temperatures and a detention time of about 1 hour to 5 days. Mesophilic conditions are preferred when the organic waste is municipal solid waste. The pH of the acid phase digester is maintained at about 4 to 8 and loading is maintained at about 0.4 to 10 lb. $VS/ft^3$-day. These conditions promote the growth of activated acid forming microorganisms. The activated hydrolytic and liquefying microorganisms are collected in digester sump 32 and pass from the digester in recirculation conduit 33. Low Btu gas, in the order of 150 to 400 Btu/SCF gas, is formed by the acid forming anaerobic culture and may be withdrawn from the acid phase digester by low Btu gas withdrawal pipe 34. Such low Btu gas may be used to supply process heat or other energy consumed in the process. The supernatant from the acid phase digester is rich in volatile fatty acids, alcohols and other solubles and is transferred to methane phase digester 40 by supernatant transfer conduit 35. If desired, some of this supernatant may be withdrawn from the acid phase digester and desired chemicals, such as acids and alcohols may be produced and/or separated and, if desired, further processed to form other desired chemicals.

Methane phase digester 40 is operated under conditions to promote the growth and action of methane forming microorganisms. The loading is about 0.01 to 1.0 lb. VS/ft$^3$-day and the digester operated at a mesophilic or a thermophilic temperature for a detention time of about ½ to 30 days. The pH of the methane phase digester is maintained between about 6.5 and 8.0. Sludge from the methane phase digester is collected in digester sump 42 and is withdrawn through sludge conduit 43 to purge the system of inhibitory substances and toxic microbial metabolites. High Btu gas, about 500 to 900 Btu/SCF gas, is withdrawn through high Btu gas withdrawal pipe 44. The high Btu gas from methane phase digester 40 has greater than 50 mole percent methane shortly after initiation of the process and increases to 60 to 70 percent or more methane after continued operation of the process, for example, after a few months of operation of the landfill. The methane containing gas produced may be upgraded by methods known to the art to provide substitute natural gas (SNG). The total digester volume, acid phase and methane phase, is preferably about 3 to 5 percent of the total volume of the bioleaching zone or landfill.

Supernatant from the methane phase reactor is rich in inorganic nutrients and organic growth factors and is withdrawn through supernatant withdrawal conduit 45 for mixing with the activated hydrolytic and liquefying microorganism culture for recirculation to the bioleaching zone. The supernatant from the methane phase digester may be passed to a mixing tank (not shown) for mixing with the activated acid forming microorganisms withdrawn from the acid phase digester for recirculation. This will provide a nutrient-rich active culture of acid forming bacteria which may be drawn upon for recirculation by recirculation conduits 21 and 22 controlled by valves 23 and 29 and necessary pumps and controls (not shown) for supplying distributor means 19 and 20, respectively, within organic material bed 10. Aqueous organic wastes such as sewage, industrial wastes, feed lot runoff, sewage or industrial sludge, may be added to the organic materials bed through the distributor means. Nutrients, pH adjusting chemicals and other desired chemicals may be added in this fashion or separately. Such wastes provides nutrients for the microorganisms and accelerated bioleaching in addition to simultaneous gasification at enhanced rates. The aqueous liquids or slurries may be provided to distributor means 19 and 20 by liquid supply conduit 24 and liquid conduit 25 feeding into distributor means 19 and 20. The flow to each of the distributor means may be controlled by valves 27 and 28 and pumps and controls (not shown). It is suitable to add to a solid organic material bed bioleaching zone about ½ to 3 weight percent (dry basis) sewage sludge slurry based upon weight of municipal solid waste as received. Thus, for example, a unified sewage sludge and municipal solid waste disposal system may be advantageously obtained in a fashion interacting to promote high energy recovery.

Further description of a landfill cell according to specific embodiments of this invention is set forth in U.S. Pat. No. 4,323,367 in FIG. 2 and the description thereof.

Figure 2:
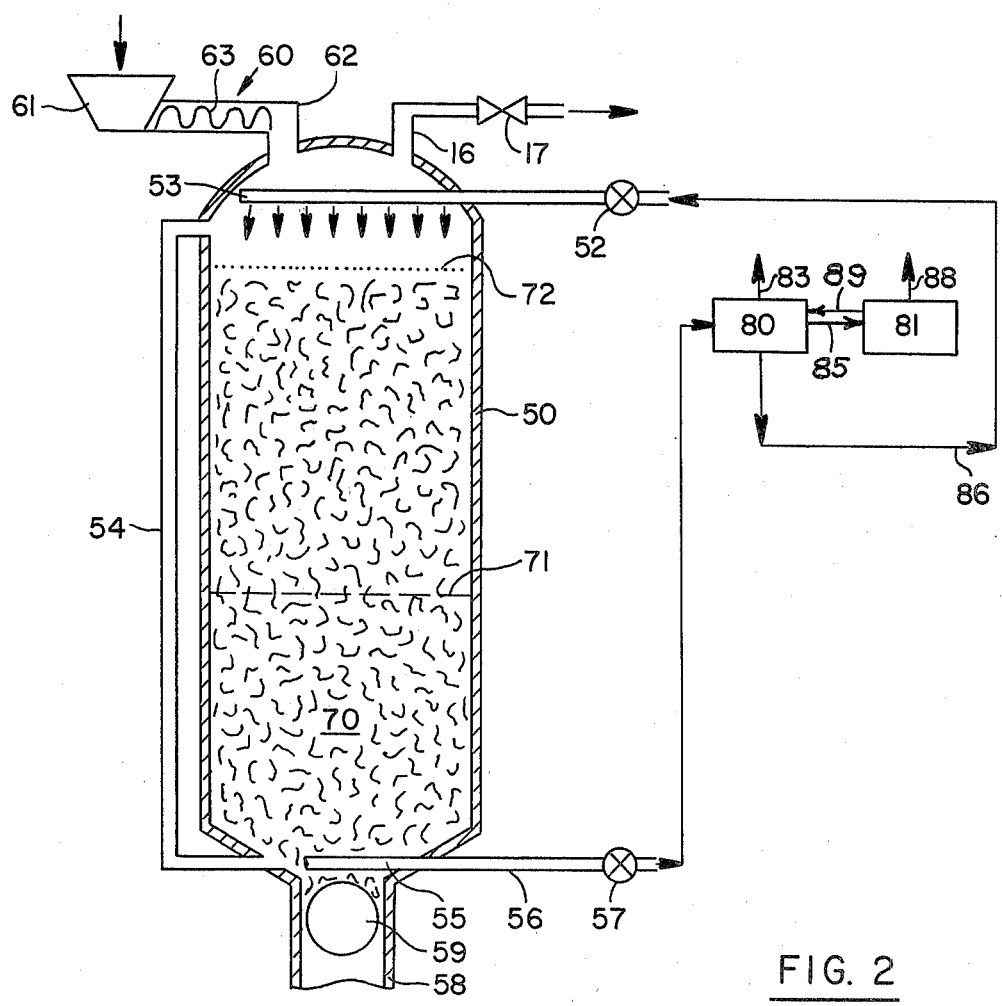
FIG. 2 is a schematic view of a portion of a bioleaching zone for operation as a partially flooded or as a fully flooded system.

FIG. 2 of this disclosure shows an embodiment of the invention wherein organic material bed 70 forming a bioleaching zone is contained within reactor vessel 50. Solid organic material is supplied to reactor vessel 50 by solids feed means 60 shown as solids storage hopper 61 and screw conveyor 63 within feed conduit 62. Any solids feed means may be used to supply organic material to form bed 70. Liquid distributor means 53 as shown in FIG. 2 is located above bed 70 and provides distribution of an activated culture of hydrolytic and liquefying anaerobic microorganisms passed from acid phase digester 80, controlled by valve means 52 through conduit 86. The supernatant from methane phase digester 81 may be passed to acid phase digester 80 through conduit 89 as shown in FIG. 2 or may be mixed with the activated culture from acid phase digester 80 for introduction to the bioleaching zone as shown by conduit 45 in FIG. 1. Supernatant from acid phase digester 80 may be passed to methane phase digester 81 through conduit 85. Bioleachate and deactivated microorganisms may be withdrawn at the bottom of bed 70 by collection means 55 and passed through conduit 56 controlled by control means 57 including suitable valving and pumping means for passage to acid phase digester 80. Solids withdrawal means 59 and solids withdrawal conduit 58 are shown in the lower portion of reactor vessel 50.

Liquid height means 54 may be any suitable means for measurement of the depth of liquid in the solid organic materials bed in a reactor vessel 50 or in a landfill, subterranean cavity or the like. In some embodiments of this invention, it is preferred to have the bioleaching zone partially flooded, as shown by liquid level 71, or fully flooded, as shown by liquid level 72. In the flooded modes of operation, it is readily apparent than the process can be conducted with upward or downward liquid flow and that the bed of organic materials may be a fixed bed or may be a moving bed in an upward, downward or lateral direction. It is also apparent that a bioleaching zone in a landfill or subterranean cavity may be likewise operated in a non-flooded, partially flooded or fully flooded mode.

In the same manner as described with respect to FIG. 1, gas comprising low methane content may be withdrawn from reactor vessel 50 through withdrawal conduit 16; low Btu gas withdrawn from acid phase digester 80 through conduit 83; and high Btu gas withdrawn from methane phase digester 81 through conduit 88.

It is seen that the application of activated acidogenic anaerobic culture on a continual basis throughout the solid organic material bed of the bioleaching zone serves to moisten the bed and promote active acid phase decomposition relatively uniformly throughout the bed. Nutrients for the acid forming anaerobes may be distributed throughout the bed on a continuous basis to encourage the hydrolytic and liquefying action of the acid forming organisms. Further, the removal of the microbial reaction products from the reaction zones throughout the bioleaching zone further rapid anaerobiosis and bioleaching of the organic material in the bed.

Any anaerobic digester and various means for increasing methane yield, gas quality and digestion kinetics such as feed pretreatment, residue post-treatment and recycling or advanced digestion modes may be used in conjunction with the process of this invention. One preferred configuration for each of the digesters in the two phase system of a preferred embodiment of this invention is shown in FIGS. 3 and 4 and the description thereof in U.S. Pat. No. 4,323,367.

FIG. 5 of U.S. Pat. No. 4,323,367, by dotted lines, shows total gas production and methane production from presently used uncontrolled sanitary municipal solid waste landfill. The bioactivity in such landfills takes place as a result of natural environmental conditions and the produced gas is withdrawn from the landfill by wells distributed throughout the landfill. It is seen that for the first several years gas production is very low and only after 9 to 10 years reaches about one-third of its total potential. Likewise, the methane fraction of the gas produced is very low, reaching only 10 percent after 5 years and about 45 percent after 10 years. The solid lines show calculated gas production from municipal solid waste landfills according to the process of the present invention. It is seen that the total gas production increases rapidly a short time after the landfill is capped, reaching over 50 percent of its total potential within 2 years and up to about 90 percent of its total potential in about 5 years. Likewise, the concentration of methane in the produced gas is in excess of 50 mole percent initially and increases to about 70 percent within the first 3 to 4 years following closing of the landfill. Practice of the process of this invention, therefore, provides a stabilized landfill which may be used for other purposes in a fraction of the time that landfills are being returned to other uses when present uncontrolled landfill practices are used.

The following example is set forth as a specific detailed illustration of one embodiment of this invention and should not be considered to limit the invention.

EXAMPLE

A laboratory size apparatus as shown in FIG. 2 was used for gas and chemical production by accelerated bioleaching of simulated municipal solid waste. A bed of organic materials having a raw weight of 39 pounds and particle sizes less than 2 inches was used as a bioleaching zone having a volume of 18.7 liters in a reactor vessel. The organic material had the following composition:

| Material | Weight Percent |
| --- | --- |
| Paper | 77 |
| Food, garden waste, etc. | 18 |
| Textiles, rags, etc. | 3 |
| Leather | 2 |

An acid phase digester and a methane phase digester were connected to each other and to the reactor vessel in the manner shown in FIG. 2. The acid phase digester was sized to accommodate an active culture volume of 25 liters and the methane phase digester sized to accommodate an active culture volume of 4.3 liters. An active anaerobic culture of acid forming microorganisms from an existing culture was transferred to the acid phase digester and an active anaerobic culture of methane forming microoganisms from an existing culture was transferred to the methane phase digester and developed to equilibrium condition. Thirty-five days after initiation of acid phase digester culture development addition of liquid from the acid phase digester to the bioleaching zone was started. Both digesters operated at mesophilic temperatures of about 35° C. Pumping of liquid through the distributor means over the bed was started and continued at the rate of 96 l/day from the settler portion of the acid phase digester which is rich in activated hydrolytic and liquefying microorganisms and aqueous organic waste or other nutrients or materials for the system adjustment or balance were added. The bioleachate was collected from the bioleaching zone and passed to the acid phase digester thus operating the bioleaching zone in a non-flooded condition. Liquid in an amount of 250 ml/day was transferred from the acid phase to the methane phase digester and 250 ml/day supernatant was transferred from the methane phase digester to the acid phase digester. The acid phase digester was a slurry phase digester and was operated at pH 4.5 to 5.5 and the methane phase digester was a packed bed of plastic Raschig rings upflow anaerobic filter operated at pH 7 to 8. The organic material bed bioleaching zone was maintained at about 35° C. The bioleaching zone was operated for 10 days in a nonflooded mode with a hydraulic detention time of 4.7 hours, based upon the empty volume of the bed. The bioleaching zone was then operated for an additional 82 days in a fully flooded mode with a hydraulic detention time of 1.2 hours. The bioleaching zone operated at about pH 5.

Gas was collected from the bioleaching zone for its full period of operation. 2.5 standard liters of gas was collected having an average composition:

87 mole percent $CO_2$
11 mole percent $CH_4$
2 mole percent $N_2$ 16 standard liters of gas was collected from the acid phase digester during bioleaching and had an average composition:

86 mole percent $CO_2$
9 mole percent $H_2$
4 mole percent $CH_4$
1 mole percent $N_2$ 67.8 standard liters of gas was collected from the methane phase digester. The gas produced in the methane digester had an average composition:

72 mole percent $CH_4$
27 mole percent $CO_2$
1 mole percent $N_2$

The methane proportion increased with time to as high as 85 mole percent.

At the time of starting liquid withdrawal from the bioleaching zone, the liquid passing in the acid phase digester contained about 6000 milligrams/liter acids and increased to a maximum of about 9000 mg/l. After 92 days of bioleaching, the acids were gasified until the acid level was down to 200 mg/l. The major acids in the leachate were acetic and propionic, the amount of propionic acid decreasing with time. The leachate was very low in iso and $C_6$ acids. Acid production increased with operation of the bioleaching zone in the fully flooded mode.

This example shows that solid organic materials can be effectively bioleached with very little gas production in the bioleaching zone; that the acid phase digester produced gases during leaching; and that leachate containing high acid concentrations produces gas of high methane content.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A process for high methane content gas production by accelerated bioleaching of solid organic materials comprising:

contacting said organic materials in a solids bed bioleaching zone with an aqueous activated culture of hydrolytic and liquefying anaerobic microorganisms under growth conditions to produce a bioleachate of hydrolysis and liquefaction products of microbial action of said microorganisms with said organic materials and to produce deactivated hydrolytic and liquefying anaerobic microorganisms;

passing said bioleachate and deactivated microorganisms from said bioleaching zone to an acid phase digestion zone operated at mesophilic or thermophilic conditions to regenerate said activated culture of hydrolytic and liquefying anaerobic microorganisms;

passing the supernatant from said acid phase digestion zone to a methane phase digestion zone operated at mesophilic or thermophilic conditions to produce gas rich in methane;

recirculating said activated culture of hydrolytic and liquefying anaerobic microorganisms from said acid phase digestion zone to said solids bed bioleaching zone; and withdrawing low Btu gas from said acid phase digestion zone and high Btu gas from said methane phase digestion zone.

2. The process of claim 1 wherein the supernatant from said methane phase digestion zone is passed to said acid phase digestion zone.

3. The process of claim 1 wherein the supernatant from said methane phase digestion zone is recirculated to said solids bed bioleaching zone.

4. The process of claim 1 wherein said solids bed bioleaching zone is non-flooded during operation.

5. The process of claim 1 wherein said solids bed bioleaching zone is partially flooded during operation.

6. The process of claim 1 wherein said solids bed bioleaching zone is fully flooded during operation.

7. The process of claim 6 wherein said aqueous activated culture is passed in upward flow through said solids bed bioleaching zone.

8. The process of claim 1 wherein said solids bed bioleaching zone comprises substantially sealed organic waste landfills.

9. The process of claim 1 wherein said solids bed bioleaching zone comprises said organic materials in an underground cavity.

10. The process of claim 1 wherein said solids bed bioleaching zone comprises said organic materials in a reactor containment vessel.

11. The process of claim 1 wherein said organic materials comprise organic refuse.

12. The process of claim 1 wherein said organic materials comprise fossil materials selected from the group consisting of peat, oil shale, tar sands, and mixtures thereof.

13. The process of claim 1 wherein a portion of said leachate is withdrawn for recovery of acids and alcohols therefrom.

14. The process of claim 1 wherein said acid phase digestion zone is operated at a pH of about 4 to 8 with loading of about 0.4 to 10 lb. VS/ft$^3$-day for detention time of about 1 to 5 days and said methane phase digestion zone is operated at a pH of about 6.5 to 8.0 with loading of about 0.01 to 1.0 lb. VS/ft$^3$-day for detention time of about ½ to 30 days.

15. The process of claim 1 wherein said aqueous activated culture of hydrolytic and liquefying anaerobic microorganisms introduced to said bioleaching zone has a pH of about 4 to 8.

16. The process of claim 1 wherein the volume of said aqueous activated culture of hydrolytic and liquefying anaerobic microorganisms and added liquid nutrient displaces the pore volume liquid in said bioleaching zone in about 1 to 5 days.

17. The process of claim 1 wherein said aqueous activated culture of hydrolytic and liquefying anaerobic microorganisms is distributed throughout said bioleaching zone by horizontal and vertical porous pipes.

18. The process of claim 1 wherein said bioleaching zone comprises an organic waste landfill comprising municipal solid waste.

19. The process of claim 1 wherein said digestion zones are operated under mesophilic conditions.

20. The process of claim 1 wherein liquid sewage sludge is mixed with said aqueous activated culture of hydrolytic and liquefying microorganisms.

21. The process of claim 1 wherein about ½ to 3 weight percent liquid sewage sludge, dry basis, based upon weight of said organic material as received is added to said bioleaching zone.

22. The process of claim 1 wherein low Btu gas, about 150 to 400 Btu/SCF, is withdrawn from said acid phase digestion zone.

23. The process of claim 1 wherein high Btu gas, about 500 to 900 Btu/SCF, is withdrawn from said methane phase digestion zone.

24. The process of claim 1 wherein said digestion zones are closed oval tubes wherein liquid is supplied to partially fill the digestion zone, passed through a liquid-gas mixing means, passed through a digestion phase, through a settler section wherein heavy portions are separated by gravity and removed from the digester, and gas is removed from the headspace and supernatant from the liquid volume.

* * * * *